US00PP20310P2

(12) United States Plant Patent

Hanes

(10) Patent No.: US PP20,310 P2

(45) Date of Patent: Sep. 15, 2009

(54) *PELARGONIUM* PLANT NAMED 'CLIP ROMEGS'

(50) Latin Name: *Pelargonium hortorum*
Varietal Denomination: Clip Romegs

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/220,352

(22) Filed: Jul. 24, 2008

(51) Int. Cl.
*A01H 5/00* (2006.01)

(52) U.S. Cl. ..... Plt./328

(58) Field of Classification Search ..... Plt./325, Plt./328

See application file for complete search history.

*Primary Examiner*—Susan B McCormick Ewoldt

(74) *Attorney, Agent, or Firm*—S. Matthew Edwards

(57) ABSTRACT

A new *Pelargonium* plant named 'Clip Romegs,' particularly distinguished by the large, light pink colored flowers with a bold red-purple blotch, dark foliage, medium vigor, and good branching.

1 Drawing Sheet

Latin name of the genus and species of the plant claimed: *Pelargonium hortorum.*

Varietal denomination: 'Clip Romegs'.

BACKGROUND OF THE NEW PLANT

The present invention comprises a new *Pelargonium,* botanically known as *Pelargonium hortorum,* and hereinafter referred to by the variety name 'Clip Romegs.'

'Clip Romegs' is a product of a planned breeding program. The new cultivar 'Clip Romegs' has large, light pink colored flowers with a bold red-purple blotch, dark foliage, medium vigor, and good branching.

'Clip Romegs' originated from a hybridization in a controlled breeding program in Gilroy, Calif. U.S.A. The female parent was an unpatented hybrid seedling identified as '9109-2.' '9109-2' has a lighter pink color, smaller blotch, less branching and vigor than 'Clip Romegs.'

The male parent of 'Clip Romegs' was an unpatented hybrid seedling identified as '9754-1.' '9754-1' has pink color with smaller flowers, lighter green foliage, and larger plant habit than 'Clip Romegs'

'Clip Romegs' was selected as one flowering plant within the progeny of the stated cross in 2004 in a controlled environment in Gilroy, Calif. U.S.A.

The first act of asexual reproduction of 'Clip Romegs' was accomplished when vegetative cuttings were taken from the initial selection in the November 2004 in a controlled environment in Gilroy, Calif. U.S.A.

Horticultural examination of plants grown from cuttings of the plant initiated in November, 2004 in Gilroy, Calif. U.S.A., and continuing thereafter, has demonstrated that the combination of characteristics as herein disclosed for 'Clip Romegs' are firmly fixed and are retained through successive generations of asexual reproduction.

'Clip Romegs' has not been observed under all possible environmental conditions. The phenotype may vary significantly with variations in environment such as temperature, light intensity and day length.

Plant Breeder's Rights for this cultivar were applied for in Canada on Aug. 23, 2007 and in Germany on Jul. 2, 2007. 'Clip Romegs' has not been made publicly available more than one year prior to the filing of this application.

DESCRIPTION OF THE PHOTOGRAPH

The accompanying photographic drawing shows typical flower and foliage characteristics of 'Clip Romegs' with colors being as true as possible with an illustration of this type. The photographic drawing shows a flowering potted plant of the new variety and a close-up of the flowers. The whole plant photograph was taken in the spring of 2006 and the close-up was taken in the spring of 2007 both in Gilroy, Calif. U.S.A. Both were grown in Gilroy, Calif. U.S.A. and were approximately 3–4 months old.

DETAILED BOTANICAL DESCRIPTION

The measurements were taken in Gilroy, Calif., in August, 2007 on plants that were growing in 14 inch containers containing 3 plants. Culture of these plants started in a greenhouse in April 2007 and were transferred to an outdoors trial in early June 2007. The plants were approximately 4 months old.

Color chart used: Royal Horticultural Society Colour Chart (R.H.S.) 2001

BRIEF SUMMARY OF INVENTION

The following observations, measurements, and comparisons describe plants grown outside in Gilroy, Calif. U.S.A. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Clip Romegs' | 'Americana Rose Splash' (U.S. Plant Pat. No. 9,306) |
|---|---|---|
| Flower color | Light pink with blotch | Rose with deeper blotch |
| Flower size | Larger | Smaller |
| Blotch | Larger | Smaller |
| Foliage color | Dark green | Medium to light green |
| Compact habit | More compact | Less compact |

Plant:

*Form, growth and habit.*—Upright, and rounded growth habit, and well branched.

*Plant height.*—8–10 cm.

*Plant height* (*inflorescence included*).—15–16 cm.

Plant width.—10–15 cm.

Foliage:

*Arrangement.*—Alternate, simple.

*Immature, leaf color, upper surface.*—RHS 137B. Lower surface: RHS 137D.

*Mature, leaf color, upper surface.*—RHS 147A. Lower surface: RHS 137D.

*Length.*—4.5–4.6 cm.

*Width.*—4.7–5.8 cm.

*Shape.*—Orbicular.

*Base shape.*—Reniform.

*Apex shape.*—Rounded.

*Margin.*—Irregularly crenate.

*Texture.*—Hirsute.

*Color of zone.*—No zone.

*Color of veins, upper surface.*—RHS 144A.

*Color of veins, lower surface.*—RHS 144A.

*Petioles color.*—RHS 144A.

*Petioles length.*—2.3–2.7 cm.

*Diameter of petiole.*—0.2–0.25 cm.

*Texture.*—Hirsute.

Stem:

*Color of stem.*—RHS 144A; with slight anthocyanin streaks of RHS 187C.

*Length of stem.*—6–7 cm.

*Diameter.*—0.5 cm.

*Length of internodes.*—About 0.5 cm.

*Texture.*—Hirsute.

Inflorence:

*Type.*—An umbel composed of 15–27 flowers and buds.

*Umbel diameter.*—9–11 cm.

*Umbel depth.*—5–6 cm.

*Color of peduncle.*—RHS 144A; with anthocyanin overlay of RHS 187A but more greyed.

*Length of peduncle.*—7.5–8 cm.

*Peduncle diameter.*—0.3–0.4 cm.

*Texture.*—Hirsute; glandular hairs of approximately between RHS 25B–C.

*Pedicel color.*—RHS 144C with overlay of anthocyanins of RHS 185A.

*Length of pedicel.*—3.4–3.7 cm.

*Diameter of pedical.*—0.2 cm.

*Texture.*—Hirsute; glandular hairs of approximately between RHS 25B–C.

Corolla:

*Form.*—Polypetalous, slightly overlapping, but with some gaps between upper and lower petals.

*Number of petals.*—5.

*Width of flower.*—5–5.3 cm.

*Color upper petals, upper surface.*—RHS 65B ground color which fades to more RHS N155B but whiter, with maturity; RHS N57A but a little deeper blotch, bleeding out to RHS N66B with very small scattered spots of between RHS N57A–B and RHS N66B; RHS N155B but whiter basally; RHS 61A veins, heavy basally.

*Color upper petals, lower surface.*—RHS N155B.

*Length of upper petals.*—2.4–2.5 cm.

*Width of upper petals.*—1.6–1.8 cm.

*Color lower petals, upper surface.*—RHS 65B ground color which fades to more RHS N155B but whiter, with maturity; RHS N57A but a little deeper blotch, bleeding out to RHS N66B with very small scattered spots of between RHS N57A–B and RHS N66B; RHS N155B but whiter basally; RHS 61B veins.

*Color lower petals, lower surface.*—RHS N155B but whiter.

*Length of lower petals.*—2.4–2.5 cm.

*Width of lower petals.*—1.7–1.8 cm.

*Petal shape.*—Obovate.

*Apex shape.*—Rounded.

*Margin.*—Entire.

*Petal texture.*—Papillose.

*Number of petaloids.*—None.

*Duration of flowering.*—Continuous flowering throughout the Summer.

Bud (just before opening):

*Color.*—Closest to RHS 53C.

*Length.*—1.5–1.6 cm.

*Width.*—0.6–0.7 cm.

*Shape.*—Elliptical.

*Number of sepals.*—5, fused at the base.

*Color of sepals.*—RHS 146B with anthocyanins basally of RHS 181B.

*Length of sepals.*—1.1–1.2 cm.

*Width of sepals.*—0.3–0.5 cm.

*Sepal shape.*—Lanceolate.

*Apex shape.*—Acute.

*Margins.*—Entire.

*Texture.*—Hirsute; pilose; glandular hairs of approximately between RHS 25B–C.

Reproductive organs:

*Pistil.*—1.

*Length.*—1.0 cm.

*Style color.*—RHS N155B but whiter.

*Style length.*—0.2–0.3 cm.

*Stigma color.*—RHS 39B.

*Number of anthers.*—About 5–6.

*Length filaments.*—0.7.

*Color of filaments.*—RHS N155B but whiter.

*Pollen amount.*—Moderate.

*Color of pollen.*—RHS N25A.

*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Clip Romegs,' substantially as illustrated and described herein.

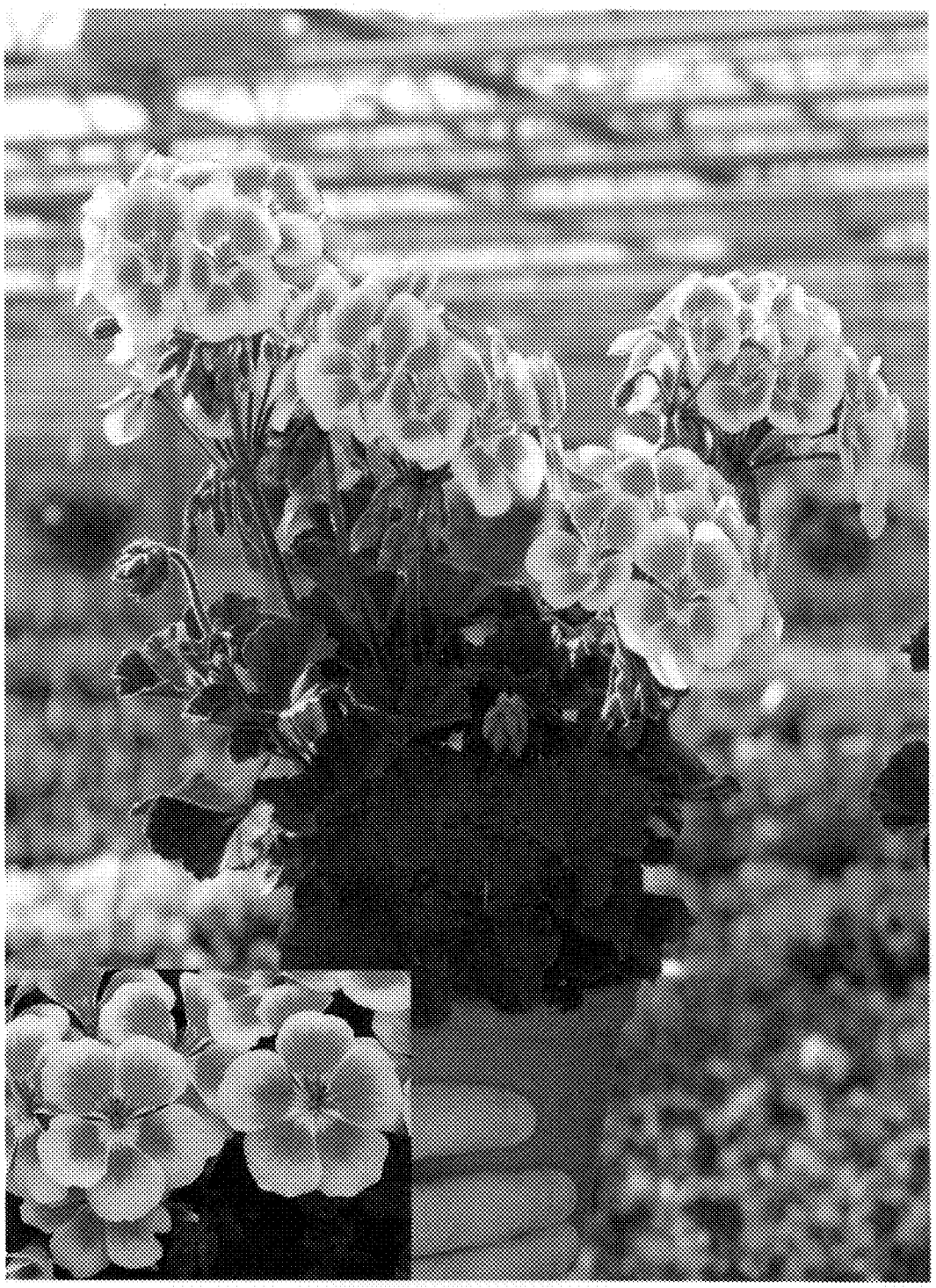

* * * * *